US00PP09167P

United States Patent [19]

Hofmann

[11] Patent Number: Plant 9,167

[45] Date of Patent: Jun. 13, 1995

[54] VARIETY OF GERANIUM NAMED 'EVENING GLOW'

[75] Inventor: Christa Hofmann, Grossdittmannsdorf, Germany

[73] Assignee: Oglevee, Ltd., Connellsville, Pa.

[21] Appl. No.: 334,853

[22] Filed: Nov. 1, 1994

[51] Int. Cl.[6] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Webb Ziesenheim Bruening Logsdon Orkin & Hanson

[57] ABSTRACT

The new cultivar is generally characterized by its dark salmon color and compact mound habit. The florets are slow to shatter and the zoned medium green foliage presents pleasing background to the inflorescence.

1 Drawing Sheet

BACKGROUND OF THE INVENTION

The present invention comprises a new and distinct cultivar of *Pelargonium*×*hortorum* known by the varietal name 'Evening Glow' (Oglevee No. 1032, Breeder No. P-318). The new variety was discovered in a selected breeding program in Dresden, Germany on May 22, 1989. The new variety is a selection from the crossing of an unidentified female parent and a group-pollination of the male parent including the PAC varieties 'Glazier Salmon' ('Lachsball', U.S. Plant Pat. No. 5,313), 'Pink Expectations' ('Palais', U.S. Plant Pat. No. 5,315), 'Rebeca' (U.S. Plant Pat. No. 7,086) and other breeding-lines. New new variety was first asexually reproduced by cuttings in Dresden, Germany on Sep. 4, 1989. The new variety has been asexually reproduced by cuttings at Oglevee, Ltd. in Connellsville, Pa. over a several year period starting on Jan. 13, 1992. It has also been trial and field tested at Connellsville and has been found to retain its distinctive characteristics through successive propagations.

The cultivar, when gron in a glass greenhouse in Connellsville, Pa. using natural light at 60° F. night and 72° F. day, has a responde time of six weeks from a rooted cutting to flowering in a 10 cm pot. The response time was determined on plants grown in soilless media employing constant fertilizer 200 parts per million of nitrogen and potassium in full light. The rooted cuttings were potted on Feb. 10, 1993 and flowered on Mar. 24, 1993.

DESCRIPTION OF THE DRAWINGS

FIG. 1 of the accompanying photographic drawing illustrates the new cultivar the color being as nearly true as possible with color illustrations of this type.

DESCRIPTION OF THE NEW PLANT

The following detailed description sets forth the characteristics of the new cultivar. The data which defines these characteristics were collected by asexual reproductions carried out by Oglevee, Ltd. in Connellsville, Pa. The plant history was taken on six week plants blossomed under natural light in a greenhouse in 15 cm pots and the color readings were taken indoors under 200–220 foot candles of fluorescent cool white light. Color references are primarily to the R.H.S. Colour Chart of The Royal Horticultural Society of London.

THE PLANT

Classification:

*Botanical.*—*Pelargonium*×*hortorum.*

*Commercial.*—Zonal florist' geranium.

Form: Compact mound form.

*Height.*—18.0–20.0 cm above media surface.

*Growth.*—Free and early flowering; basal branching.

Strength: Stands upright without artificial support.

Foliage: Stalked leaf attachment; zone present.

Leaves:

*Size.*—8.0–9.5 cm across; fully expanded leaf.

*Shape.*—Reinform; cordate base.

*Margin.*—Crenate.

*Texture.*—Slightly reflective; slightly pubescent.

*Color.*—Top: Green Group 137B. Bottom: Yellow-Green Group 146B. Zone: Yellow-Green Group 147A.

*Ribs and Veins.*—Palmate venation. Color: Yellow-Green Group 147C.

Petioles:

*Color.*—Yellow-Green Group 146B.

*Length.*—8.0–10.0 cm.

Stem:

*Color.*—Yellow-Green Group 146C.

*Internodes.*—2.5–4.5 cm in length.

THE BUD

Shape: Upright hemispherical cluster.

Size: 2.5–3.5 cm across.

INFLORESCENCE

Blooming habit: Semi-double; slow to shatter.

Size: 13.0–15.5 cm across; fully open bloom.

Borne: Umbel; florets on pedicel; pedicel on peduncle; 6.0–9.0 cm above foliage canopy.

Florets:

*Form.*—Flat to slightly cupped; petaloids present.

*Color.*—Top: Red Group 41C with edges of petals being Red Group 41D. Bottom: Red Group 38A.

*Petals.*—Obovate; margin entire; separate, not united; smooth flat to slightly cupped; 6–8 in number.

*Size.*—5.0–5.5 cm across.

*Texture and appearance.*—Smooth; Apppearance from a distance is a deep salmon pink with a zoned medium green foliage.

Petaloids:

*Quantity.*—1–3 in number.

*Shape.*—Flat, twisted; some tubular; some with pollen attached.

*Color.*—Top: Red Group 41D. Bottom: Red Group 38A.

Pedicel:

*Length.*—3.0–4.0 cm in length.

*Color.*—Tip (stipule end): Red-Purple Group 59B. Base (peduncle end): Yellow-Green Group 146C.

Peduncle: 13.5–19.0 cm in length.

*Color.*—Yellow-Green Group 146C. Arises from the node opposite the leaf petiole.

Disease resistance: Not known.

REPRODUCTIVE ORGANS

Stamens:

*Anthers.*—2.0–3.0 mm in length.

*Filaments.* 7.0–8.0 mm in length.

*Pollen.*—Golden brown.

Pistils:

*Number.*—1.

*Length.*—8.0–9.0 mm.

*Stigma.*—5–6 parted; red purple.

*Style.*—3.0–4.0 mm in length.

Ovaries: Superior; pubescent; pale green; 4.0–5.0 mm in length.

Fruit: None observed.

GENERAL CHARACTERISTICS

'Evening Glow' brings a new dark salmon color to the geranium industry. This new variety exhibits a compact mound habit, a continuous show of color and performs well in the garden. The dark zone is an eye pleasing accent to the medium green foliage and rich salmon color.

I claim:

1. A new and distinct variety of geranium plant substantially as shown and described.

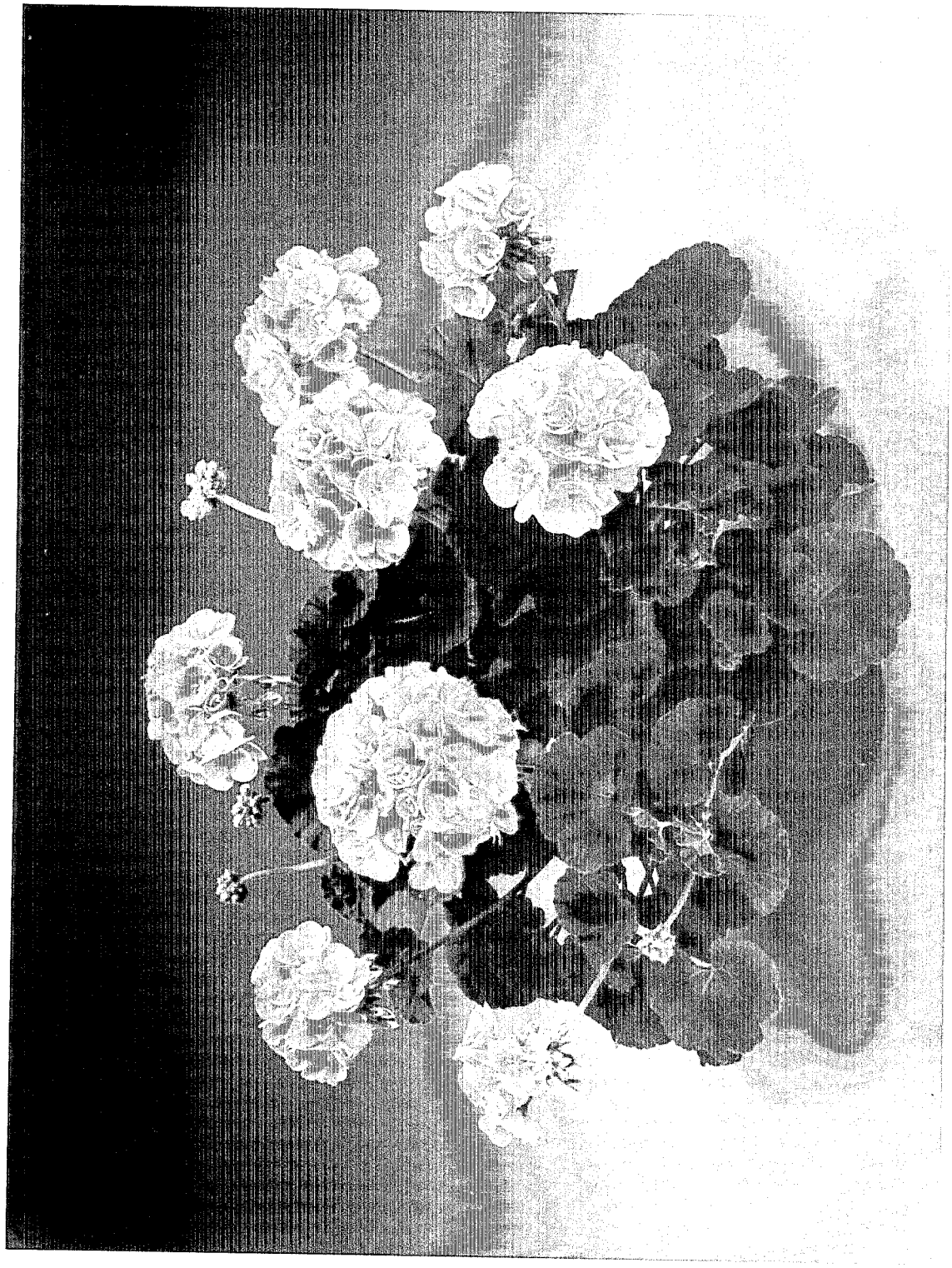

* * * * *